(12) United States Patent
Bruheim et al.

(10) Patent No.: US 9,068,142 B2
(45) Date of Patent: Jun. 30, 2015

(54) REDUCED FLUORIDE CRUSTACEAN OIL COMPOSITIONS

(71) Applicant: Olympic Seafood AS, Fosnavaag (NO)

(72) Inventors: Inge Bruheim, Volda (NO); Mikko Griinari, Espoo (FI); Stig Rune Remoy, Fosnavaag (NO)

(73) Assignee: OLYMPIC SEAFOOD AS (NO)

( * ) Notice: Subject to any disclaimer, the term of this patent is extended or adjusted under 35 U.S.C. 154(b) by 36 days.

(21) Appl. No.: 13/856,642

(22) Filed: Apr. 4, 2013

(65) Prior Publication Data

US 2013/0225794 A1 Aug. 29, 2013

Related U.S. Application Data

(60) Division of application No. 13/342,664, filed on Jan. 3, 2012, now Pat. No. 8,557,297, which is a continuation of application No. 13/063,488, filed as application No. PCT/NO2009/000322 on Sep. 14, 2009.

(30) Foreign Application Priority Data

Sep. 12, 2008 (NO) .................................... 20083906

(51) Int. Cl.
| | |
|---|---|
| C07K 1/00 | (2006.01) |
| C11B 3/00 | (2006.01) |
| A23L 1/015 | (2006.01) |
| A23L 1/305 | (2006.01) |
| A23L 1/33 | (2006.01) |
| A23L 1/30 | (2006.01) |
| A23L 1/325 | (2006.01) |
| A23D 9/013 | (2006.01) |
| A23J 1/04 | (2006.01) |
| C07K 14/435 | (2006.01) |
| C07K 19/00 | (2006.01) |
| A23J 3/34 | (2006.01) |
| A23D 9/007 | (2006.01) |
| A23D 9/02 | (2006.01) |
| C11B 1/10 | (2006.01) |
| C11B 1/02 | (2006.01) |

(52) U.S. Cl.
CPC ............... *C11B 3/006* (2013.01); *A23L 1/0153* (2013.01); *A23L 1/3053* (2013.01); *A23L 1/33* (2013.01); *A23L 1/3006* (2013.01); *A23L 1/3252* (2013.01); *A23D 9/013* (2013.01); *A23J 1/04* (2013.01); *A23L 1/0152* (2013.01); *C07K 14/43509* (2013.01); *C07K 19/00* (2013.01); *A23J 3/34* (2013.01); *A23D 9/007* (2013.01); *A23D 9/02* (2013.01); *C11B 1/10* (2013.01); *C11B 1/104* (2013.01); *C11B 1/025* (2013.01)

(58) Field of Classification Search
None
See application file for complete search history.

(56) References Cited

U.S. PATENT DOCUMENTS

| | | | |
|---|---|---|---|
| 6,555,155 | B2 | 4/2003 | Saxby et al. |
| 6,800,299 | B1 * | 10/2004 | Beaudoin et al. ............. 424/522 |
| 2008/0274203 | A1 | 11/2008 | Brunheim et al. |
| 2011/0217386 | A1 | 9/2011 | Jansson |
| 2011/0224450 | A1 | 9/2011 | Sclabos Katevas et al. |

FOREIGN PATENT DOCUMENTS

| | | |
|---|---|---|
| EP | GB 2240786 | 8/1991 |
| EP | 0785029 B1 | 5/2001 |
| JP | 2909508 | 6/1999 |
| WO | WO00/23546 | 4/2000 |
| WO | WO02/102394 | 12/2002 |
| WO | WO2008/060163 A1 | 5/2008 |

OTHER PUBLICATIONS

Miniadis-Meimaroglou et al., Chemistry and Physics of Lipids, 2008, vol. 152, p. 104-112.*
Neptune Krill oil supplement facts, NOW supplements, downloaded on Aug. 18, 2014 from nowfoods website , 2 pages.*
Vazhiyil Venugopal, "Marine Products for Healthcare: Functional and Bioactive Nutraceutical Compounds from the Ocean", CRC Press, Oct. 20, 2008—Technology & Engineering—p. 248 ONLY.*
Marcias-Sanchez at al., "Extraction of carotenoids and chlorophyll from microalgae with supercritical carbon dioxide and ethanol and cosolvent," *J. Sep. Sci.*, 31:1352-1362 (2008).
Miniadis-Mcimaroglu at al., "Isolation and identification of phospholipids molecular species in a wild marine shrimp *Penaeus kerathurus* muscle and cephalothorax," *Chemistry and Physics of Lipids*, 152:104-112 (2008).
Slizyte et al., "Enzymatic hydrolysis of cod (*Gadus morhua*) by-products optimization of yield and properties of lipid and protein fractions," *Process Biochemistry*, 40:3680-3692 (2005).
Turgut at al., "Extraction of Phospolipids from Canola with Supercritical Carbon Dioxide and Ethanol," *JAOCS*, 72(9):1009-1015 (1995).
Yamaguchi, "Supercritical Carbon Dioxide Extraction of Oils form Antartic Krill," *J. Agric. Food Chem*, 34(5): 904-907 (1986).
Yoshitomi et al., "Effect of total replacement of dietary fish meal by low fluoride krill (*Euphausia superba*) meal on growth performance of rainbow trout (*Oncorhynchus mykiss*) in fresh water," *Aquaculture*, 266:219-225 (2007).

* cited by examiner

*Primary Examiner* — Kade Ariani
(74) *Attorney, Agent, or Firm* — Medlen & Carroll, LLP (57) ABSTRACT

The present invention contemplates the creation of a low fluoride oil processed from a phospholipid-protein complex (PPC) formed immediately upon a crustacean (i.e., for example, krill) catch. The process comprises disintegrating the crustaceans into smaller particles, adding water, heating the result, adding enzyme(s) to hydrolyze the disintegrated material, deactivating the enzyme(s), removing solids from the enzymatically processed material to reduce fluoride content of the material, separating and drying the PPC material. Then, using extraction with supercritical $CO_2$ and ethanol as solvents, inter alia krill oil is separated from the PPC. In the extraction the krill oil can be separated almost wholly from the feed material. The products have low fluoride content. The manufacturing costs in the extraction process are relatively low.

6 Claims, 4 Drawing Sheets

REDUCED FLUORIDE CRUSTACEAN OIL COMPOSITIONS

RELATED APPLICATIONS

This application is a Divisional of copending application Ser. No. 13/342,664 filed on Jan. 3, 2012 which is a continuation-in-part of application Ser. No. 13/063,488 filed on May 24, 2011 which claims priority to PCT/NO2009/000322 filed on Sep. 14, 2009, which has priority to NO 20083906 filed on Sep. 12, 2008.

FIELD OF THE INVENTION

The invention relates to a method for processing crustaceans (i.e., for example, krill) rich in lipids to produce low fluoride compositions comprising phospholipids, proteinaceous nutrients and oil (i.e., for example, neutral lipids and/or triglycerides).

BACKGROUND OF THE INVENTION

The crustaceans, especially krill, represent a vast resource as biological material. The amount of Antarctic krill (*Euphausia superba*), depending on the calculation method and investigation, is roughly 1 to $2 \times 10^9$ tons and the possible weight of the annual catch is estimated at 5 to $7 \times 10^6$ tons. These small crustaceans, which live in the cold waters around the Antarctic, are interesting as a source for proteins, lipids such as phospholipids, poly-unsaturated fatty acids etc., chitin/chitosan, astaxanthin and other carotenoids, enzymes and other materials.

Several methods for isolating above-mentioned materials have been developed. One problem is that the products may contain unwanted trace material included in the exoskeleton (also called integument or cuticle) of the crustaceans. For example, krill accumulates fluoride in their exoskeleton, thereby increasing the fluoride amount of any produced material either through the inclusion of parts of the exoskeleton or through extraction processes not taking into account the transfer of fluoride to the final material. In this case free fluoride or loosely bound fluoride may diffuse from the exoskeletal material and into the further processed material, making the end product high in fluoride ions and/or fluorinated compounds.

Fluoride is a compound that in high concentrations is detrimental for the health of land-dwelling animals as well as all kind of fish and crustaceans and especially fresh-water fish species, since fluoride atoms have the tendency of entering into the bone structure of such organisms and creating fluorosis, or weakening of the bone structure similar in its effect to osteoporosis, but different since it is the bone structure itself, and not the porosity of the bone that is affected. Skeletal fluorosis is a condition characterized by skeletal abnormalities and joint pain. It is caused by pathological bone formation due to the mitogenic action of fluoride on osteoblasts. In its more severe forms, skeletal fluorosis causes kyphosis, crippling and invalidism. Secondary neurological complications in the form of myelopathy, with or without radiculopathy, may also occur. High fluoride intake has also been shown to be toxic to the male reproductive system in rat experiments, and in humans high fluoride intake and symptoms of skeletal fluorosis have been associated with decreased serum testosterone levels. Consequently, if krill material is used as a starting material for food or feed products, precautions have to be taken for removing fluoride through the processing steps. However, the diffusion of fluoride and the presence of miniscule particles of the exoskeleton represent a problem that is difficult to overcome when processing krill material in an industrial scale.

Polar lipids such as phospholipids are essential for cell membranes and are also called membrane lipids. For most known animal species the content of polar lipids is nearly constant. However, this does not hold for the Antarctic krill. The phospholipids content varies from 2% up to 10% depending on the season. The high content, e.g. more than 5%, of the phospholipids is in principle good, but means also a problem, because it may result in strong emulsions in industrial processes. The emulsions complicate the separation of the lipid and proteinaceous fractions in the processes, such as hydrolysis.

The krill oil is one the valuable products made from krills. It contains inter alia phospholipids, triglycerides and carotenoid astaxanthin while being essentially free of protein, carbohydrates and minerals. Different portions of the krill material are separated from each other by, inter alia: i) crushing krill mechanically; ii) pressing them, iii) hydrolysis with heat and enzymes; iv) centrifugal force in rotating devices; and v) solvent extraction.

What is needed in the art are significant improvements to these rather conventional approaches and are described within many embodiments of the present invention (infra). For example, a disintegrated raw crustacean material may be separated and/or extracted into various enriched low-fluoride crustacean meal and/or oil compositions.

SUMMARY

The invention relates to a method for processing crustaceans (i.e., for example, krill) rich in lipids to produce low fluoride compositions comprising phospholipids, proteinaceous nutrients and oil (i.e., for example, neutral lipids and/or triglycerides).

In one embodiment, the present invention contemplates a phospholipid-peptide complex (PPC) composition comprising a range between approximately 40-50% lipids and less than 0.5 mg/Kg fluoride. In one embodiment, the lipids comprise phospholipids.

In one embodiment, the present invention contemplates an oil composition comprising approximately 400-500 grams/Kg phospholipids, approximately 200-260 grams/Kg Omega-3 fatty acids, less than 0.5 mg/Kg fluoride, approximately 15 grams/Kg lysophosphatidic acid, and less than approximately 8 grams/Kg free fatty acids.

In one embodiment, the present invention contemplates a de-oiled phospholipid-peptide complex (PPC) composition comprising approximately 300-400 grams/Kg lipids, wherein approximately 0.1-1.0% are free fatty acids and a range between approximately 22-27% (w/w) that are Omega-3 fatty acids. In one embodiment, the lipids comprise phospholipids.

In one embodiment, the present invention contemplates a crustacean lipid composition comprising at least 75% phospholipids. In one embodiment, the lipid composition comprises between approximately 75%-90% phospholipids. In one embodiment, the lipid composition comprises between approximately 75%-80% phospholipids.

In one embodiment, the present invention contemplates a dried protein hydrolysate composition comprising approximately 70-80% protein, approximately 1.5-3.0% lipids, and approximately 5-7% ash.

In one embodiment, the present invention contemplates a method, comprising: a) providing; i) a hydrolyzed and disintegrated crustacean material; ii) at least one horizontal centrifuge capable of separating said hydrolyzed crustacean material; and iii) a fluid comprising a non-polar solvent; and b) separating said hydrolyzed crustacean material into a high fluoride solid fraction and a low fluoride hydrolyzed material fraction with a first horizontal centrifuge; c) separating said low fluoride hydrolyzed material fraction into a phospholipid-peptide complex (PPC) composition subfraction and a concentrated hydrolysate subfraction with a second horizontal centrifuge; and d) contacting said PPC composition subfraction with said non-polar solvent, wherein a low fluoride oil is extracted. In one embodiment, the disintegrated crustacean material has particle sizes between approximately 1-25 millimeters. In one embodiment, the first horizontal centrifuge avoids emulsification of said hydrolyzed crustacean material. In one embodiment, the non-polar solvent comprises supercritical $CO_2$. In one embodiment, the contacting further comprises a non-polar solvent. In one embodiment, the non-polar solvent is ethanol. In one embodiment, the second horizontal centrifuge comprises an extended separation pathway. In one embodiment, the contacting is performed at a pressure of less than 300 bar. In one embodiment, the non-polar solvent further extracts a de-oiled PPC composition from said PPC composition subfraction. In one embodiment, the ethanol separates a phospholipid composition and a protein hydrolysate composition from said de-oiled PPC composition. In one embodiment, the de-oiled PPC is separated from the PPC in less than ten hours. In one embodiment, the de-oiled PPC is separated from the PPC in less than five hours. In one embodiment, the de-oiled PPC is separated from the PPC in less than two hours. In one embodiment, the hydrolyzed crustacean material comprises hydrolyzed krill material. In one embodiment, the separating said hydrolyzed crustacean material is performed at a centrifugal force of between approximately 1,000-1,800 g. In one embodiment, the separating said low fluoride hydrolyzed material fraction is performed at a centrifugal force of between approximately 5,000-10,000 g. In one embodiment, the method produces a phospholipid-peptide complex (PPC) composition comprising a range between approximately 40%-50% lipid and less than 0.5 mg/Kg fluoride. In one embodiment, the method produces an oil composition comprising approximately 400-500 grams/Kg phospholipids, approximately 200-260 grams/Kg Omega-3 fatty acids, less than 0.5 mg/Kg fluoride, approximately 15 grams/Kg lysophosphatidic acid, and less than approximately 8 grams/Kg free fatty acids. In one embodiment, the method produces a de-oiled phospholipid-peptide complex (PPC) composition comprising approximately 300-400 grams/Kg lipids, wherein approximately 0.1-1.0% are free fatty acids and a range between approximately 20-28% (w/w) are Omega-3 fatty acids. In one embodiment, the method produces a crustacean lipid composition comprising at least 75% phospholipids. In one embodiment, the lipid composition comprises a range between approximately 75%-90% phospholipids. In one embodiment, the lipid composition comprises a range between approximately 75%-80% phospholipids. In one embodiment, the method produces a dried protein hydrolysate composition comprising approximately 70-80% protein, approximately 1.5-3.0% lipids, and approximately 5-7% ash.

In one embodiment, the present invention contemplates a system comprising: a) a solvent unit comprising at least non-polar solvent inlet; b) an extraction tank unit in fluidic communication with the solvent unit, wherein the tank comprises an inlet configured to receive a phospholipid-protein complex composition; c) a separator unit comprising an outlet configured to release a low fluoride oil composition and residual co-solvent, wherein the separator is in fluidic communication with the tank; d) an absorbent unit in fluidic communication with the separator unit, wherein the absorbent unit is capable of recycling the non-polar solvent. In one embodiment, the non-polar solvent is a supercritical fluid. In one embodiment, the supercritical fluid comprises carbon dioxide. In one embodiment, the solvent unit further comprises a co-solvent inlet. In one embodiment, the co-solvent is a polar solvent. In one embodiment, the polar solvent is ethanol. In one embodiment, the at least one non-polar solvent inlet comprises an unused non-polar solvent inlet. In one embodiment, the at least one non-polar solvent inlet comprises a recycled non-polar solvent inlet. In one embodiment, the solvent unit further comprises a fluid pump. In one embodiment, the tank unit is pressurized by the fluid pump. In one embodiment, the solvent unit further comprises a heater. In one embodiment, the phospholipid-protein complex composition in the tank unit is heated by the heater. In one embodiment, the separator outlet is in fluid communication with an evaporator. In one embodiment, the separator further comprises a horizontal centrifuge. In one embodiment, the horizontal centrifuge is a decanter centrifuge having an extended separation pathway. In one embodiment, the phospholipid-protein complex composition is a low fluoride crustacean phospholipid-protein complex composition. In one embodiment, the low fluoride crustacean phospholipid-protein complex composition is a low fluoride krill phospholipid-protein complex composition.

In one embodiment, the present invention contemplates a method for processing crustaceans, especially krills, in which method the crustaceans are disintegrated into smaller particles, fresh water is added to the disintegrated material, the water with the disintegrated material is heated and enzyme(s) are added for hydrolyzing the disintegrated material and said enzyme(s) is/are deactivated, the method further comprising steps: a) removing solids from the hydrolyzed material to reduce fluoride content of the material; b) separating phospholipid-peptide complex material and concentrated hydrolysate fraction from each other; c) drying said phospholipid-peptide complex material; and d) dividing the drying result, or PPC, to components by extraction(s) using at least a supercritical $CO_2$ as solvent, wherein the processing of crustaceans is started as soon as a crustacean catch has been raised on ship. In one embodiment, the fluoride content solids are removed from the hydrolyzed material by a decanter. In one embodiment, the phospholipid-peptide complex material and concentrated hydrolysate fraction are separated from each other by a sedicanter with high centrifugal forces and long clarification/separation zones to avoid an emulsification. In one embodiment, the method further comprises using in the extraction ethanol as a co-solvent in addition to the supercritical $CO_2$ to separate: i) a krill oil consisting of phospholipids and triglycerides, or neutral oil, and ii) a protein hydrolysate from the PPC. In one embodiment, the pressure of the solvent being at most 300 bar. In one embodiment, the extraction includes two steps: i) first using only the supercritical $CO_2$ as solvent to separate de-oiled PPC from the PPC; and ii) second using only ethanol as solvent to separate phospholipids and protein hydrolysate from the de-oiled PPC. In one embodiment, the duration of the step when said de-oiled PPC is extracted from the PPC is at most three hours. In one embodiment, the method produces a phospholipid-peptide complex (PPC) composition comprising approximately 40%-50% lipid and approximately 0.5 mg/kg fluoride. In one embodiment, the lipid comprises phospholipids. In one embodiment, the method produces an oil composition comprising approximately 400-500 grams/Kg phospholipids, approximately 200-260 grams/Kg Omega-3 fatty acids, approximately 0.5 mg/Kg fluoride, approximately 15 grams/Kg lysophosphatidic acid, and less than approximately 8 grams/Kg free fatty acids. In one embodiment, the method produces a de-oiled phospholipid-peptide complex (PPC) composition comprising approximately 300-400 grams/Kg lipids, wherein approximately 0.1-1.0% are free fatty acids and approximately 22-27% (w/w) are Omega-3 fatty acids. In one embodiment, the method produces a crustacean phospholipid composition comprising approximately 75% polar lipids. In one embodiment, the method produces a dried protein hydrolysate composition comprising approximately 70-80% protein, approximately 1.5-3.0% lipids, and approximately 5-7% ash.

DEFINITIONS

The term "disintegrated material" as used herein refers to any biological material that has been subjected to a mechanical destruction and/or disruption that results in a composition having particle sizes of between approximately 1-25 millimeters, preferably between approximately 3-15 millimeters, more preferably between approximately 5-10 millimeters and most preferably approximately 8 millimeters.

The tem "hydrolyzed material" as used herein refers to any biological material that has been subjected to high heat and/or enzymatic treatment. Such hydrolyzed materials would be expected to have phospholipid/peptide components that are physically separated from the components of the chitinous exoskeleton.

The term "crustacean" as used herein refers to any marine organism have a hard outside shell (e.g., a chitinous exoskeleton combined with a carbonate) encompassing a fleshy interior that is a living organism. More specifically, the crustaceans are usually considered a large class of mostly aquatic arthropods that have a chitinous or calcareous and chitinous exoskeleton, a pair of often much modified appendages on each segment, and two pairs of antennae. For example, a crustacean may include but not limited to, krill, lobsters, shrimps, crabs, wood lice, water fleas, and/or barnacles.

The term "horizontal centrifuge" refers to any device that is capable of rotating a mixture in the Z-plane (as opposed to the X-plane and/or Y-plane as with conventional centrifuges). This rotation is generated by a screw-type conveyor element aligned horizontally within a tube shaped enclosure. The induced centrifugal force then layers the heavier particles to the outside edges of the enclosure, while the lighter particles form layers closer to the center of the enclosure. Some horizontal centrifuges are modified to comprise an extended separation pathway and induce high gravitational forces (e.g., a sedicanter).

The term "polar solvent" as used herein refers to any compound, or compound mixture, that is miscible with water. Such polar solvent compounds include, but are not limited to, ethanol, propanol and/or ethyl acetate.

The term "non-polar solvent" as used herein refers to any compound, or compound mixture, that is not miscible with water. Such non-polar solvent compounds include, but are not limited to, hexane, pentane and/or supercritical $CO_2$.

The term "supercritical $CO_2$" refers to any mixture comprising carbon dioxide ($CO_2$) in a fluid state while held at, or above, its critical temperature and critical pressure where its characteristics expand to fill a container like a gas but with a density like that of a liquid. More specifically, carbon dioxide becomes a supercritical fluid above 31.1° C. and 72.9 atm/ 7.39 MPa. Carbon dioxide usually behaves as a gas in air at standard temperature and pressure (STP), or as a solid called dry ice when frozen. If the temperature and pressure are both increased from STP to be at or above the critical point for carbon dioxide, it can adopt properties midway between a gas and a liquid. As contemplated herein, supercritical $CO_2$ can be used as a commercial and industrial solvent during chemical extractions, in addition to its low toxicity and minimal environmental impact. The relatively low temperature of the process and the stability of $CO_2$ also allows most compounds (i.e., for example, biological compounds) to be extracted with little damage or denaturing. In addition, because the solubility of many extracted compounds in $CO_2$ may vary with pressure, supercritical $CO_2$ is useful in performing selective extractions.

The term "fluoride" as used herein interchangeably and refer to any compound containing an organofluoride and/or an inorganic fluoride.

The term "high fluoride solid fraction" as used herein refers to a composition containing the vast majority of a crustacean's exoskeleton following a low g-force (e.g., between approximately 1,000-1,800 g) horizontal centrifugation separation of a hydrolyzed and disintegrated crustacean material. This fraction contains small particles of exoskeleton of the crustacean that retains the vast majority of fluoride (i.e., for example, between 50-95%) in these organisms.

The term "low fluoride" as used herein may refer to the product of any method and/or process that reduced the fluoride from the original material by approximately 10-fold (i.e., for example, from 5 ppm to 0.5 ppm). For example, 'a low fluoride crustacean phospholipid-protein complex' comprises ten-fold less fluoride than 'a low fluoride hydrolyzed and disintegrated crustacean material'.

The term "low fluoride hydrolyzed material fraction" as used herein refers to a composition containing the vast majority of a crustacean's fleshy internal material following a low g-force (e.g., between approximately 1,000-1,800 g) horizontal centrifugation separation of a hydrolyzed and disintegrated crustacean material. This fraction contains small particles of phospholipids, neutral lipids, proteins and/or peptides that is largely devoid of any fluoride (i.e., for example, between 5%-50% of the raw hydrolyzed and disintegrated material).

The term "a low fluoride phospholipid-peptide complex composition subfraction" as used herein refers to a low fluoride composition containing the vast majority of lipid material following a high g-force (e.g., between approximately 5,000-10,000 g) horizontal centrifugation separation of a low fluoride hydrolyzed material fraction.

The term "concentrated hydrolysate composition subfraction" as used herein refers to a low fluoride composition containing the vast majority of water soluble lean material following a high g-force (e.g., between approximately 5,000-10,000 g) horizontal centrifuge separation of a low fluoride hydrolyzed material fraction.

The term "low fluoride oil" as used herein refers to a lipid-rich composition created by the extraction of a phospholipid-peptide complex composition subfraction using a selective extraction process, such as with a supercritical carbon dioxide fluid. Such a process removes approximately ten-fold of the fluoride from the raw hydrolyzed and disintegrated crustacean material.

The term "de-oiled phospholipid-peptide complex" as used herein refers to a low fluoride composition containing the vast majority of dry matter composition created by the extraction of a phospholipid-peptide complex composition subfraction using selective extraction process, such as a supercritical carbon dioxide fluid.

The term "phospholipid composition" as used herein refers to a low fluoride composition comprising a high percentage of polar lipids (e.g., approximately 75%) created by the extraction of a de-oiled phospholipid-peptide complex using a co-solvent, such as ethanol.

The term "protein hydrolysate" as used herein refers to a low fluoride composition comprising a high percentage of protein (e.g., approximately 70-80%) created by the extraction of a de-oiled phospholipid-peptide complex using a co-solvent, such as ethanol.

The term "immediately" as used herein refers to a minimum practical period between decking a crustacean catch in a trawl bag and/or net coupled with a direct transfer to a suitable disintegraor. For example, this minimum practical period should preferably not exceed 60 minutes, more preferred to not exceed 30 minutes, even more preferred to not exceed 15 minutes.

The term "hydrolysis" as used herein refers to any break and/or disruption made in a protein structure of a disintegrated crustacean material, wherein in the naturally occurring protein sequences become shorter (i.e., for example, by breaking peptide bonds of the amino acid sequence primary structure) and/or denatured (i.e., for example, an unfolding of the amino acid sequence secondary, tertiary and/or quaternary structure). This process may be controlled by hydrolytic enzyme(s). For example, one or more exogenous proteolytic enzymes (e.g. alkalase, neutrase, and enzymes derived from microorganisms or plant species) may be used in the process. Co-factors such as specific ions can be added depending on the used enzymes. The selected enzyme(s) can also be chosen for reducing emulsions caused by high content of phospholipids in the raw material. Besides the temperature, the hydrolysis takes place within optimal or near-optimal pH and sufficient time. For example, the exogenous enzyme alkalase the optimum pH is about 8, optimum temperature about 60° C. and the hydrolysis time 40-120 minutes.

The term "solvent unit" refers to any enclosed volume configure to heat and pressurize a mixture of supercritical carbon dioxide fluid and/or a co-solvent (e.g., ethanol). Such an enclosed volume may be constructed out of any suitable material including but not limited to metals (e.g., steel, aluminum, iron etc.), plastics (e.g., polycarbonate, polyethylene etc.), fiberglass (etc.).

The term "extraction tank" refers to any enclosed volume configured to withstand heat and pressure sufficient to perform lipid and protein extraction from a raw biomass using a supercritical carbon dioxide fluid. As designed, the extraction tank contemplated herein is configured such that the solvents containing the extracted lipids and proteins rise to the tank top for transfer to a separator unit. Such an enclosed volume may be constructed out of any suitable material including but not limited to metals (e.g., steel, aluminum, iron etc.), plastics (e.g., polycarbonate, polyethylene etc.), fiberglass (etc.).

The term "separator unit" refers to any enclosed volume configured with a centrifuge capable of separating the components of the extracted lipids and proteins received from an extraction tank. The respective extraction components exit the separator unit via outlet ports such that the remaining solvents (i.e., supercritical $CO_2$) are transferred to an absorbent unit for recycling. Such an enclosed volume may be constructed out of any suitable material including but not limited to metals (e.g., steel, aluminum, iron etc.), plastics (e.g., polycarbonate, polyethylene etc.), fiberglass (etc.).

The term "absorbent unit" refers to any enclosed volume configured with materials that will remove contaminants from a supercritical $CO_2$ fluid. Such materials may include, but are not limited to charchol, coal, purifying gases, plastic polymer resins and/or filtration cartridges comprising single or dual-flat extruded nets (Tenax UK LTD, Wrexham, North Wales LL13 9JT, UK). Such an enclosed volume may be constructed out of any suitable material including but not limited to metals (e.g., steel, aluminum, iron etc.), plastics (e.g., polycarbonate, polyethylene etc.), fiberglass (etc.).

The term "in fluidic communication" refers to any means by which a fluid can be transported from one location to another location. Such means may include, but are not limited to pipes, buckets and/or troughs. Such means may be constructed out of any suitable material including but not limited to metals (e.g., steel, aluminum, iron etc.), plastics (e.g., polycarbonate, polyethylene etc.), fiberglass (etc.).

DETAILED DESCRIPTION OF THE INVENTION

The invention relates to a method for processing crustaceans (i.e., for example, krill) rich in lipids to produce low fluoride compositions comprising phospholipids, proteinaceous nutrients and oil (i.e., for example, neutral lipids and/or triglycerides).

Krill oil comprises lipids extracted with solvents from krill biomass. Krill biomass can be either fresh, whole krill (WO2008/060163A1), frozen whole krill (Neptune Technologies & Bioresources Inc., Canada), lyophilized whole krill (JP2215351) or krill meal (US20080274203). Solvents used in extracting lipids from krill biomass have been reported as acetone+ethanol (WO2000/23546; WO2002/102394), ethanol+hexane (Enzymotec Ltd), ethanol alone (JP2215351; Aker BioMarine ASA, Norway) or supercritical $CO_2$+ethanol co-solvent (US2008/0274203; WO2008/060163). Solvent-free technology for obtaining krill oil has also been developed (US20110224450A1). Krill oil comprises a lipid fraction of raw krill biomass that is essentially free of protein, carbohydrates and/or minerals. Krill oil also comprises neutral lipids (e.g., mostly triglycerides), polar lipids (e.g., mostly phospholipids) and carotenoid astaxanthin. Although it is not necessary to understand the mechanism of an invention, it is believed that the lipid and/or fatty acid compositions of krill oil vary depending of the season. Phosphatidylcholine is the largest phospholipid component of krill oil and its proportion is relatively stable.

In some embodiments, the present invention contemplates methods of processing crustacean biomass having unexpected findings including, but not limited to: i) removal of most of the exoskeleton from the crustacean biomass that results in low level of fluorides in PPC and very low levels of fluoride in krill oil extracted from PPC by supercritical CO2 and ethanol co-solvent; ii) a level of fluorides in the crustacean oil that is less than 0.5 ppm in contrast to conventional krill oil with fluoride content of greater than 0.5 to 5 ppm; iii) crustacean oil extracted from PPC by supercritical $CO_2$ and ethanol co-solvent has a minimal brown color suggesting that minimal degradation of astaxanthin or formation of tertiary oxidation products has occurred; iv) it is believed that the level of dark/brown color measured on Hunter L* a b scale and the pyrrole content measured by absorption at 570 nm are lower in the low fluoride, supercritical $CO_2$ and ethanol co-solvent extracted crustacean oil as compared to the conventional krill oil; v) analysis of the low fluoride, supercritical $CO_2$ and ethanol co-solvent extracted crustacean oil indicates a minimal content of FFA and LPC. These findings suggest that the lipids of crustacean biomass have undergone minimal hydrolysis during the initial processing steps producing PPC; and vi) levels of FFA in the low fluoride, supercritical $CO_2$ and ethanol co-solvent crustacean oil are less than 0.8 g/100 oil and LPC content less than 1.5 g/100 g of oil.

I. Historical Overview of Crustacean Processing Methods

Publication GB 2240786 discloses a method for processing krill including removing a part of the fluoride content of krill. The removing is based on passing electric current through pulverized krill. However, fluoride-containing solid particles remain in the material.

Publication US 2011/0224450 (Sclabos Katevas et al., herein incorporated by reference) discloses a method for obtaining krill oil from whole raw krills using inter alia cooking, separating by decanter, and pressing. No solvents and extraction are used.

Publication WO 2008/060163 (Pronova Biopharma AS) discloses a method for obtaining krill oil using supercritical $CO_2$ and either ethanol, methanol, propanol or isopropanol as co-solvent. Fresh or pre-heated (about 90° C.) whole krills are used as the extraction feed material.

Publication WO 02/102394 (Neptune Technologies & Bioresources) discloses a method for obtaining krill oil using in different phases acetone and ethanol or e.g. ethyl acetate as solvents. Frozen whole krill is used as feed material.

Publication JP 2215351 (Taiyo Fishery) discloses a method for obtaining krill oil using ethanol as solvent. Lyophilized whole krills are used as feed material.

Publication US 2008/0274203 (Aker Biomarine ASA, Bruheim et al.) (herein incorporated by reference) discloses a method for obtaining krill oil from krill meal using supercritical fluid extraction in a two-stage process. Stage 1 removes the neutral lipid by extracting with neat supercritical $CO_2$ or $CO_2$ plus approximately 5% of a co-solvent. Stage 2 extracts the actual krill oils using supercritical $CO_2$ in combination with approximately 20% ethanol.

There are a number of problems associated with these conventionally known technologies of extracting krill lipids, including but not limited to: i) whole crustacean biomass contains high fluoride exoskeleton particles that results in the production of fluoride-contaminated crustacean oil; ii) crustacean oil having a brownish hue color may arise from exposing astaxanthin to excessive heat during crustacean biomass processing. Specifically, brown color can arise from degradation of astaxanthin and/or from accumulation of the end products of non-enzymatic browning (e.g., Strecker degradation products or polymerized pyrroles). Brown color resulting from this non-enzymatic process is believed to result from oxidative degradation due to a reaction of secondary lipid oxidation products with amino groups from amino acids or proteins creating so-called tertiary oxidation products; iii) freezing the crustacean biomass for transportation to an extraction plant. Frozen crustacean biomass can be relatively stable, but some changes in the product are known to occur over time. For example, one characteristic change in frozen krill is partial hydrolysis of the lipids resulting in accumulation of free fatty acids (FFA) arising from both triglycerides and phospholipids and lysophospholipids, specifically lysophosphatidylcholine (LPC), arising from hydrolysis of phosphatidylcholine; iv) the use of heat and frozen storage can induce oxidation of lipids and proteins in crustacean biomass. Primary oxidation leads into formation of secondary oxidation products that are volatile and can be detected in krill oil as off-flavors or undesirable odor; and v) the separation of the krill oil from the feed material is quite inefficient, wherein only about a half of the oil can be extracted.

II. Production of Low Fluoride Crustacean Materials

In one embodiment, the present invention contemplates a method comprising forming a phospholipid-peptide complex (PPC) composition from a crustacean (i.e., for example, krill) immediately after the catch has been brought upon on board a boat and/or ship (i.e., for example, a fishing vessel). The process of creating the PPC composition comprises disintegrating the crustaceans into a disintegrated material comprising smaller particles (i.e., for example, between approximately 1-25 millimeters), adding water, heating the disintegrated material, adding enzyme(s) to hydrolyze the disintegrated material, deactivating the enzyme(s), removing solids (i.e., for example, exoskeleton, shell, and/or carapace) from the enzymatically processed material to reduce the fluoride content of the material, separating and drying the PPC composition. Preferably, the PPC composition is transferred to an on-shore facility (i.e., for example, a fish oil extraction plant) where a low-fluoride crustacean oil is separated from the PPC composition using solvents including, but not limited to, supercritical $CO_2$ and/or ethanol. Using alternative extractions, de-oiled PPC compositions, phospholipids and/or protein hydrolysate compositions are also separated from the PPC composition.

An advantage of some embodiments of the invention is that these crustacean products, like krill oil, have a low fluoride content. This is due to the fact that the solid crustacean exoskeletal particles (i.e., for example, shell and/or carapace) are effectively removed from mass to be processed.

Another advantage of the invention is that crustacean oil can be separated effectively, almost completely, from the disintegrated crustacean material (e.g., feed material) during the extraction. This is due to the fact that, in the extraction process with the supercritical $CO_2$ solvent, the feed material comprises a PPC composition. Although it is not necessary to understand the mechanism of an invention, it is believed that the phospholipids of the feed material are embedded in a matrix of hydrolyzed protein which means that the close association between the phospholipids and hydrophobic/phosphorylated proteins is broken thus facilitating the extraction of the lipids.

An advantage of the invention is that relatively low pressure and temperature can be used in the extraction, which means lower production costs.

A further advantage of the invention is that disposal of residual solvents, common when using other more conventional lipid solvents, is avoided when using supercritical $CO_2$ as a solvent.

A further advantage of the invention is that also the phosphatidylserine (PS), free fatty acids (FFA) and lysophosphocholine (LPC) contents are very low in the end products.

A further advantage of the invention is that a low fluoride crustacean oil product (i.e., for example, a low fluoride krill oil) has very little brown color. It is believed in the art that appearance of a brown color in crustacean oil indicates that unfavorable processes are occurring during the manufacture of the feed material (e.g., a disintegrated crustacean material).

A. Processing of Crustaceans

The present invention provides an industrial method for processing catches of crustaceans comprising a number of steps beginning with a very early and substantially complete removal of the crustacean's exoskeleton (i.e., for example, the crust, carapace and/or shell). Although it is not necessary to understand the mechanism of an invention, it is believed that the crustacean exoskeleton comprises a vast majority of fluoride in the organism. Consequently, this step thereby results in a substantial removal of fluoride from the crustacean material. The method also uses longitudinal centrifugation techniques that prevents separation problems caused by emulsions when processing a raw material with high content of phospholipids.

The method according to the present invention is initiated immediately after decking a catch of crustacean. It is of importance that the method according to the present invention is initiated as soon as possible after the crustacean catch has been decked since fluoride starts to leak/diffuse immediately from the exoskeleton into the crustacean's flesh and juices.

When using the term "immediately" in connection with starting the process according to the present invention this relates to the period from decking the crustacean catch and to the initial disintegration of the crustacean (see infra). This period of time should be kept to a minimum, and should preferably not exceed 60 minutes, more preferred not exceed 30 minutes, even more preferred not exceed 15 minutes, and should include a direct transfer of the krill catch from the trawl bag and/or net to a suitable disintegrator. A disintegrator of the crustacean material may be a conventional pulping, milling, grinding or shredding machine.

The crustacean catch is initially loaded into a disintegration apparatus where the crustacean catch is subjected to pulping, milling, grinding and/or shredding to create a disintegrated crustacean material. The temperature of the disintegration process is around the ambient temperature of the water, i.e. between −2 and +1° C., preferably around +0° C. to +6° C., and may be performed by any convenient disintegration method. This disintegration process is also conventionally done by the previous known processing methods, and represents one of the obstacles according to the prior art because it produces large amounts of exoskeletal particles from the crustacean mixing in the milled material and producing a disintegrated paste with a high fluoride content. However, this high fluoride content is one of the reasons why the prior art processed crustacean material has limited applications and is less suitable for food, feed or corresponding food or feed additives compared to other marine raw materials e.g. pelagic fish.

According to the present invention the crustacean material is divided into a particle size suitable for a further separation step for not interfering with the subsequent processing steps. The disintegrating process is performed continuously and produces particle sizes up to 25 mm, a preferred particle size range is between approximately 0.5-10 mm and a more preferred size range is between approximately 1.0-8 mm.

Although it is not necessary to understand the mechanism of an invention, it is believed that this small particle size distribution represents one of advantages of the present invention because the fluoride has a tendency to leak out of the milled material and mingle with the rest of the raw material. However, this leaking process takes time and is not rapid enough to negatively impact a subsequent enzymatic hydrolysis step, provided the hydrolysis step is performed within specific parameters with respect to time and optimal, or near-optimal conditions, such as pH and temperature and optionally with the addition of co-factors such as specific ions depending on the used enzymes.

The temperature of the disintegrated material may, according to the present invention, be elevated to a temperature suitable for the subsequent enzymatic hydrolysis. Preferably, the temperature may be increased within seconds (e.g. 1-300 seconds, more preferred 1-100 seconds, even more preferred 1-60 seconds, most preferred 1-10 seconds) subsequent to the disintegrating step for reducing the processing time and thereby preventing diffusion of fluoride and for preparing the material for the enzymatic hydrolysis.

According to the present invention enzymes may be added directly to the disintegrated material or through the added water or both, before, during or after the disintegration process.

According to the present invention, exogenous proteolytic enzymes (e.g., alkalase, neutrase, enzymes derived from microorganisms including, but not limited to, *Bacillus subtilis* and/or *Aspergillus niger*, and/or or enzymes derived from plant species) may be added before, during or after the disintegration, and before, during or after the heating of the disintegrated material. The added enzyme(s) may be in the form of one single enzyme or a mixture of enzymes. The conditions of the hydrolysis should match the optimal hydrolytic conditions of the added enzyme(s) and the selection of optimal conditions for the selected exogenous hydrolytic enzyme(s) is known to the person skilled in the art. As an example, the exogenous enzyme alkalase having a pH optimum of about 8, a temperature optimum of 60° C. and a hydrolysis time of 40-120 minutes. The selected enzymes, or combination of enzymes, should also be chosen for reducing emulsions caused by high content of phospholipids in the raw material.

An efficient amount of proteolytic enzyme(s) will be set after a process- and product optimization process that depends upon the efficiency of a specific chosen commercial enzyme or mix of enzymes. A typical amount by weight of commercial enzymes, as a ratio of the amount of the weight of the disintegrated raw material, are preferably between 0.5% and 0.05%, more preferably between 0.3% and 0.07% and most preferable between 0.2% and 0.09%. This hydrolysis step is aided by endogenous (natural) enzymes because rapid and uncontrolled autolysis is well known in fresh caught crustaceans.

The reason for adding exogenous enzymes is to take control of, and guide, the breakdown of the proteinaceous material in the disintegrated substance as well as speeding up/accelerating the hydrolysis of the material to avoid and/or preclude the leaking of fluoride from the shell, carapace and crust as mentioned supra. These hydrolytic enzymes, or a combination of hydrolytic enzymes, should also be carefully chosen to reduce emulsion in the production process. Enzymes may be selected from exo- and/or endopeptidases. If a mixture of enzymes is used, such a mixture may also include one or more chitinases for subsequently making the chitin-containing fraction(s) more amenable to further downstream processing. If chitinases are used, care must be taken for not increasing the leakage of fluoride from the shell/crust/carapace of the crustacean into the other fractions. However, since such fluoride leakage takes time, it is possible to perform such an enzymatic treatment within the time parameters indicated supra. A more convenient alternative to including chitinases in the enzyme mix of the initial hydrolysis step will be to process the separated chitin-containing fraction subsequently to the separation step.

As it is important to avoid the leaking of fluoride from the milled exoskeletal material into the milled fleshy material, and since the leaking to some degree is related to the increased surface area created through the disintegrating step, the enzymatic hydrolysis step should be finished within a time interval of 100 minutes, preferably within 60 minutes, most preferred within 45 minutes calculated from the addition of the endogenous enzyme(s). The amount of enzyme(s) added is related to the type of enzyme product used. As an example it may be mentioned that the enzyme alkalase may be added in an amount of 0.1-0.5% (w/w) of the raw material. This should be taken into context with the added endogenous enzymes since the addition of more enzymes will reduce the time interval of the hydrolytic step. As mentioned supra the time of the hydrolytic step is one of the crucial features of the present process since a short hydrolysis time reduces the diffusion time of fluoride from particles of the exoskeleton. The hydrolytic enzymatic processing step is intended to remove the binding between the soft tissue of the krill to the exoskeleton of the crustacean.

Subsequent to, or together with, the hydrolytic processing step the hydrolyzed and distinegraed crustacean material is passed through a particle removal device operating through a gravitational force such as a longitudinal centrifuge (i.e., for example, a decanter). This first separation step removes the fine particles containing a considerable amount of the fluoride from the hydrolysed or hydrolysing crustacean material to create a solids fraction. The centrifuge is operated with a g force between 1,000 and 1,800 g, more preferably between 1,200 and 1,600 g and most preferably between 1,300 and 1,500 g. Through this particle removal step a substantial amount of fluoride is removed from the proteinaceous crustacean fraction. The reduction of fluoride on a dry weight basis as compared to conventional crustacean meal, with a typical fluoride content of 1,500 p.p.m, may be up to 50%, even more preferred up to 85%, most preferred up to 95%.

The enzymatic hydrolysis may be terminated by heating of the hydrolysing material (incubate) to a temperature over 90° C., preferably between 92-98° C. and most preferred between 92-95° C., prior to, during or after the separation step, as long as the hydrolysis duration lies within the above given boundaries. The hydrolysis is terminated before, during, or after the fine particle removal step, most preferred after the fine particle removal step. The temperature of the first centrifugation particle removal step, in one embodiment, depend on the optimal activity temperature of the enzyme (in the case where the enzymatic hydrolysis step is terminated by heating after the fine particle separation step).

The fluoride content in the prior art processed krill protein material has limited applications and are less suitable for food or feed or corresponding food or feed additives, as mentioned supra but the fluoride content of the removed exoskeletal material is not preventive for further separation/purification of this fraction. Thus materials such as chitin, chitosan and astaxanthin may be isolated from the separated exoskeletal material. Such isolation procedures are known within the art. Steps may also be taken for removing the fluoride from the isolated exoskeletal material e.g. through dialysis, nanofiltration, through electrophoresis or other appropriate technologies.

Hydrolytic enzyme(s) deactivation may be performed in different ways, such as adding inhibitors, removing co-factors (e.g., crucial ions through dialysis), through thermal inactivation and/or by any other deactivating means. Among these, thermal inactivation, as mentioned supra, is preferred by heating the proteinaceous material to a temperature where the hydrolytic enzymes become denatured and deactivated. However, if a product where the relevant native proteins are not denatured is wanted, other means than heating for deactivating the hydrolytic enzymes should be selected.

A first centrifugation forms a de-fluorinated hydrolyzed and disintegrated crustacean material fraction and a solids fraction (e.g., containing high fluoride exoskeleton particles). As described below, the low flourine hydrolyzed and disintegrated crustacean material fraction may be subsequently separated (e.g., by a second centrifugation) to form a low fluoride Phospholipid-Peptide Complex (PPC) composition fraction, a lean low fluoride Concentrated Hydrolysate Fraction (CHF) fraction that can be used as a food and/or feed additives, and a lipid fraction mainly consisting of neutral lipids. The PPC composition subfraction is rich in lipids, like a smooth cream with no particles, wherein the lipids are well suspended within the peptide components. This suspension results in small density differences between the different PPC composition components thereby making it difficult to further separate the PPC composition with common centrifugal separators and/or decanters. This is especially accentuated with crustacean catches during the second half of the fishing season.

Ordinary disc centrifugal separators (i.e., generating rotational force in the X and Y plane) do not work properly to separate a PPC composition subfraction into its respective components since emptying and necessary cleaning cycles with water will disturb separation zones. Conventional centrifugation separation processes result in the formation of unwanted emulsion products having a high phospholipid content and low dry matter concentrations. Standard decanters cannot separate the PPC composition subfraction into its respective components due to a low g force limitation, short separation zone and an intermixing of light and heavy phases at the discharge of heavy phase from the machine.

In one embodiment, the present invention contemplates a method comprising separating a low fluoride PPC material into subfractions using a horizontal decanter centrifuge with an extended separation path. See, FIG. 2. Horizontal centrifuges (e.g., generating a rotational force in the Z plane) are useful for the present invention comprise modified convention decanter centrifuges. For example, a PPC composition subfraction would enter an ordinary decanter from a bowl through a central placed feed pipe in the middle of the separation zone. In contrast, when using horizontal centrifuges as contemplated herein, the PPC composition subfraction enters at the end and at the opposite side of the outlet (1). This modification provides a significant improvement in the separation process by providing a considerably longer clarification/separation zone than ordinary decanters and utilizes the total available separation length (2) of the machine. The drive is able to impart high g-forces: 10,000 g for small machines and 5,000 to 6,000 g for high capacity machines, facilitating the separation of very fine, slow-settling PPC composition subfractions without the complications of emulsification. The PPC composition subfraction will be subjected to the highest g-force just before entering under the baffle (3). The different liquid layers separated from PPC composition subfraction are concentrated gradually along the axis of the horizontal centrifuge thereby exiting the machine under baffle (3) by the g force pressure generated by the machine (4). The separation of the PPC composition subfraction into a layer comprising about 27-30% dry matter makes the downstream processing efficient in terms of operating/robustness and as well economically considering both yield and costs of preparing the dry matter into a meal composition. The PPC composition subfraction separation also creates a layer comprising a lean hydrolysate that can be evaporated into a concentrated hydrolysate of greater than 60%.

B. Processing of Krill

One embodiment according to the invention is depicted as a flow diagram for the processing of krill (steps 11 to 1A). See, FIG. 1. The function according to the method, or the process according to the invention is initiated as soon as a krill catch has been raised to the ship. Although it is not necessary to understand the mechanism of an invention, it is believed that fluoride immediately starts to leak/diffuse from the chitinous exoskeleton into the flesh and juices of the dead krills. 'As soon as' means here a period at most 60 minutes, in practice, for example 15 minutes. During this period the krill catch is transferred from the trawl/net to a suitable disintegrator. In the disintegrator the krill material is crushed to relatively small particles. The disintegrating can be performed by any convenient method: pulping, milling, grinding or shredding. The temperature in the disintegration process is around the ambient temperature of the water, i.e. between −2° C. and +10° C., preferably between +0° C. and +6° C. The disintegration produces large amount of chitinous debris among the rest of the krill material, thereby contributing to a high fluoride content.

The particle size distribution of the disintegrated krill material is significant because of the above-mentioned fluoride leak from the chitinous debris to the rest of the raw material. It is believed that the smaller particle sizes results in a more complete separation of the solids fraction from the disintegrated krill material (infra). For this reason the preferable range of the particle size is 1.0-8 mm. However, the leaking process is relatively slow and has not time to be realized during the following process phases.

Figure 1:
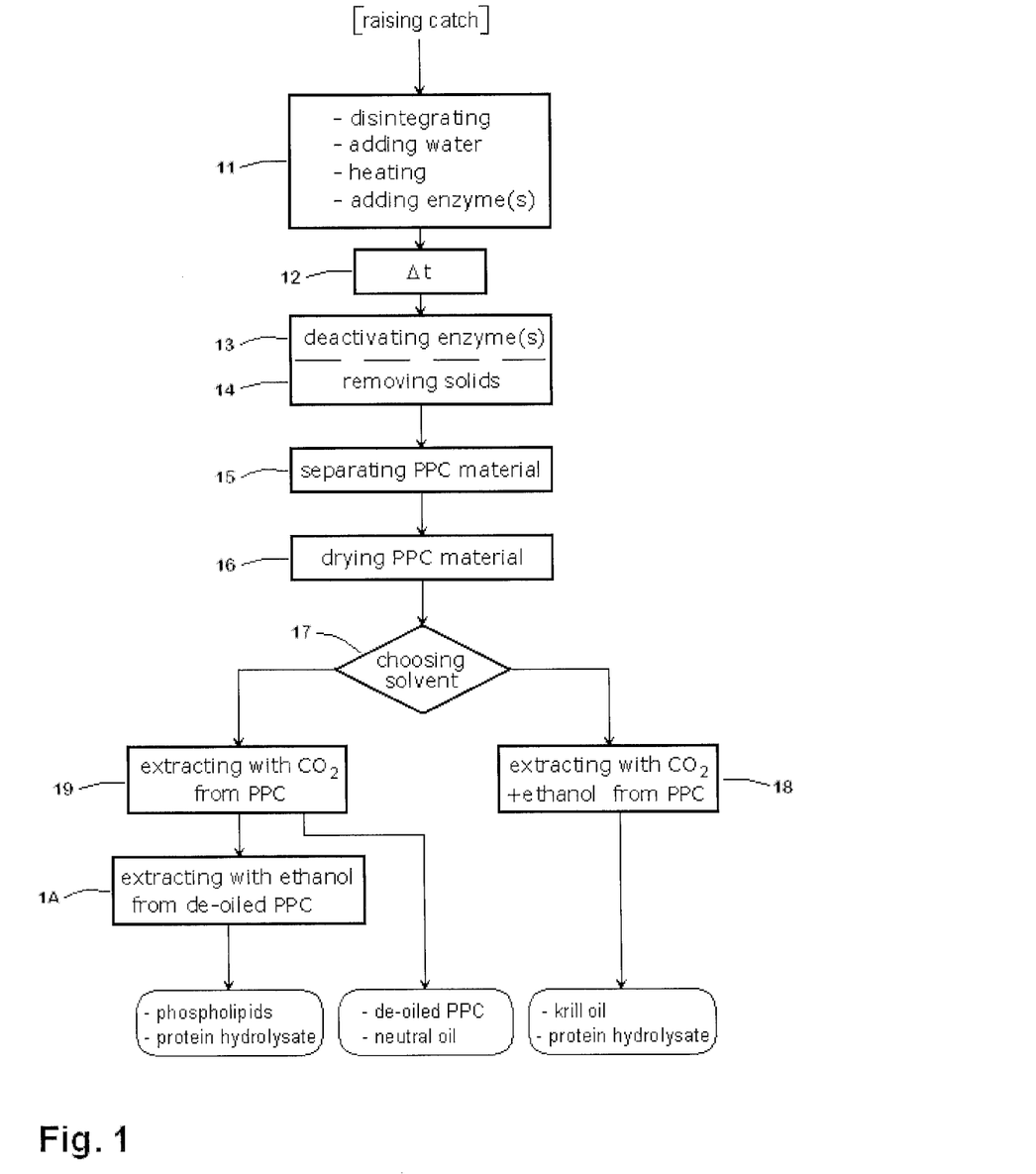
FIG. 1 presents a flow diagram of one embodiment of a method to produce a low fluoride crustacean material.

Next, including in steps 11, fresh water is added to the disintegrated krill material. The volume/L of the water added is, for example, same as the weight/kg of the disintegrated krill material to be processed during the subsequent process phase of enzymatic hydrolysis. The temperature of the disintegrated krill material with the added water is increased such that it is suitable for the hydrolysis and enzyme(s) are added. The heating is carried out fast, within at most five minutes, after the disintegrating step to reduce the processing time and thereby to prevent diffusion of fluoride and to prepare the material for the enzymatic hydrolysis. The enzyme(s) can be added directly to the disintegrated krill material, or through the added water or both, before, during or after the heating step.

The term "hydrolysis" as used herein, means that breaks are made in the protein structure in the disintegrated substance, and the protein chains become shorter. This process is controlled by hydrolytic enzyme(s). For example, one or more exogenous proteolytic enzymes (e.g. alkalase, neutrase, and enzymes derived from microorganisms or plant species) may be used in the process. Co-factors such as specific ions can be added depending on the used enzymes. The selected enzyme(s) can also be chosen for reducing emulsions caused by high content of phospholipids in the raw material. Besides the temperature, the hydrolysis takes place within optimal or near-optimal pH and sufficient time. E.g. for the exogenous enzyme alkalase the optimum pH is about 8, optimum temperature about 60° C. and the hydrolysis time 40-120 minutes.

The amount of proteolytic enzyme(s) can be set after a process- and product optimization, and depends naturally on the efficiency of the chosen enzyme or mix of enzymes. A typical ratio of the weight of added commercial enzymes to the weight of the disintegrated krill material is between 0.05% and 0.5%, preferably between 0.1% and 0.2%. Fresh caught krill is known for rapid and uncontrolled autolysis, or the destruction of the cells by endogenous (natural) enzymes, for which reason the treatment described here has to be proceeded without delays when the catch is not frozen.

The enzymatic hydrolysis also causes removing the bindings between the soft tissue of the krill and the exoskeleton. If a mixture of enzymes is used, the mixture may also include one or more chitinases to facilitate the further processing of the chitin-containing fractions. Chitinases are enzymes that break down glycosidic bonds in chitin.

The enzymatic hydrolysis is finished within 100 minutes from the addition of the endogenous enzyme(s). The preferred duration Δt of the hydrolysis is shorter, for example 45 minutes (phase 12). Relatively short hydrolysis duration is important, because in that case the diffusion of the fluoride from the exoskeleton particles to the other material is reduced.

The hydrolysis is stopped by deactivating the hydrolytic enzyme(s), method step 13. There are many ways to deactivate the enzymes. Here it is used the thermal one: the temperature of the enzymatically processed material is increased over 90° C., preferably between 92-98° C., in which case the hydrolytic enzymes become denatured. In practice the deactivating of the hydrolytic enzyme(s) can be performed also during or after the solid particle removal.

In step 14, the solid particles (e.g., krill exoskeleton) are removed from the enzymatically hydrolyzed and disintegrated krill material by passage through a device based on the centrifugal force such as a conventional horizontal centrifuge and/or decanter. Although it is not necessary to understand the mechanism of an invention, it is believed that these solid particles, or solids, originate from the exoskeleton of krills and, as mentioned, contain a considerable amount of the fluoride. The decanter is operated with a force between 1,000 and 1,800 g, preferably between 1,300 and 1,500 g. Through this particle removal step a substantial amount of fluoride, more than 90%, is removed from the krill material. The temperature in the decanter is for example 90° C., and if the deactivation of the enzyme(s) is done after the removal of solids, the temperature in the decanter is then increased to e.g. 93° C.

Next, in step 15 the hydrolyzed and disintegrated krill material with low fluoride content is modified by passage through an extended separation path horizontal centrifuge (i.e., for example, a sedicanter). See, FIG. 2. In the sedicanter, the hydrolyzed and disintegrated krill material, is separated into the valuable fatty portion, or PPC (Phospholipid-Peptide Complex) material fraction, and a CHF portion (Concentrated Hydrolysate Fraction).

Figure 2:
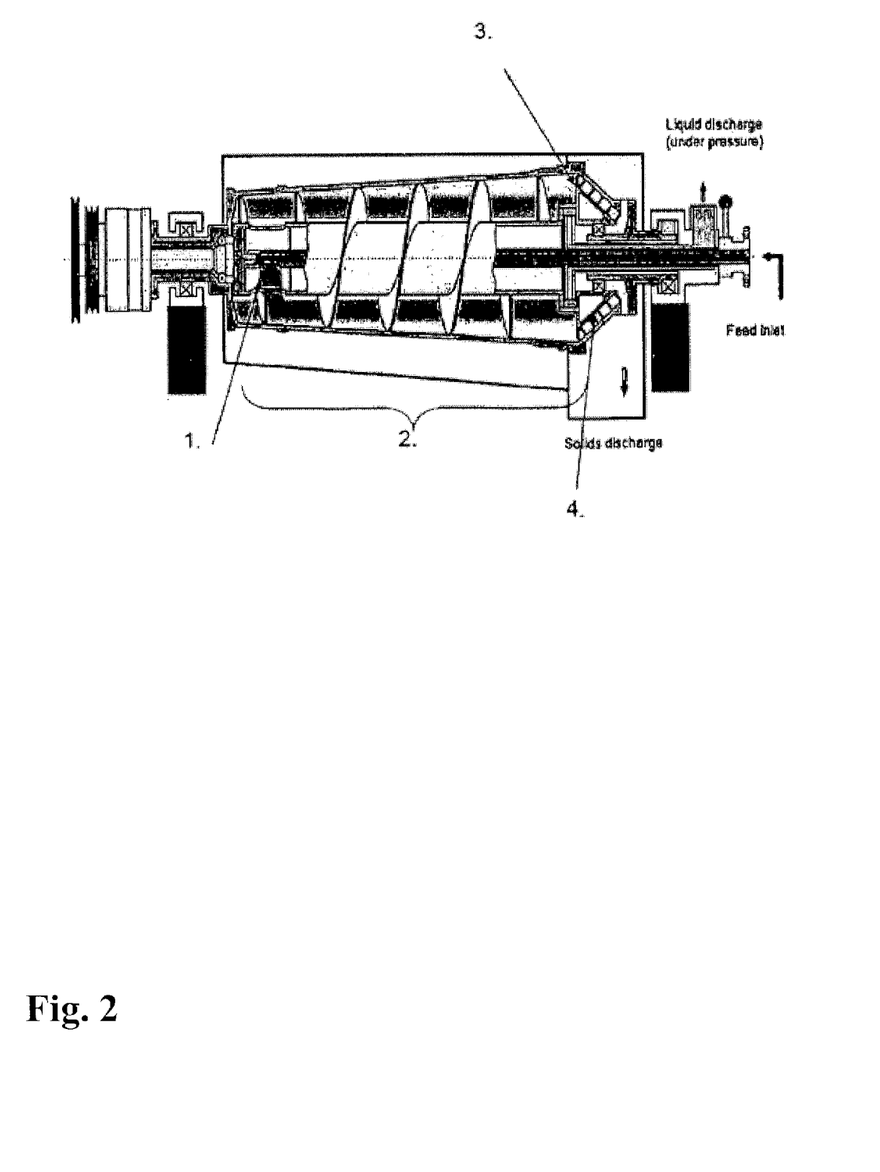
FIG. 2 presents a longitudinal centrifuge with an extended separation path. This specific example is a FLOTTWEG SEDICANTER horizontal decanter centrifuge.

The separation of hydrolyzed and disintegrated krill material into the PPC material is difficult because of the small density differences within the krill material. The sedicanter is a modified horizontal centrifuge including a long horizontal clarification/separation zone and generating high centrifugal forces (5,000 to 6,000 g). These features facilitate the separation of fine, slow-settling PPC without emulsification. The latter is a problem in the ordinary centrifuges with short separation zone and lower forces, and in which water is used in emptying and cleaning cycles. The dry matter concentration of PPC material, pressured out from the sedicanter, is about 27-30%.

In the following step 16 the PPC material is dried to a meal to avoid the lipid oxidation. The drying process is gentle with low temperature (0-15° C., preferably 2-8° C.) and inert conditions, which give a reduced oxidative stress on the long-chain poly-unsaturated omega-3 fatty acids. A lyophilisation process would also be suitable since this avoids an overheating of the product.

The PPC meal, or more briefly PPC, is then packed in air tight bags under nitrogen atmosphere for later direct use and continuation process.

A typical mass balance of the processed raw lean Antarctic krill is shown below in Table I:

TABLE I

Typical Mass Balance Of Antarctic Krill

| Matter | From 500 kg raw krill + water | Dry weight |
|---|---|---|
| Wet PPC material | 80 kg | 28% |
| PPC meal | 25 kg | 97% |
| Hydrolysate | 770 kg | 6% |
| CHF | 78 kg | 60% |
| Fluoride-containing particles | 45 kg | 40% |
| Neutral oils | <5 kg | |

The fluoride content in the hydrolyzed and disintegrated krill material is 1.2 g/kg, whereas in the PPC it is at most 0.5 g/kg and typically 0.3 g/kg. Thus, about two thirds of the fluoride has been removed.

When the PPC is further processed, components may be isolated by an extraction. In this phase, a solvent may be used (step 17 in FIG. 1). For example, to obtain krill oil from the PPC, supercritical $CO_2$ and/or ethanol may be utilized, either separately or in combination. The extraction process (step 18) yields, in addition to the krill oil, a protein hydrolysate.

Compressing and heating a material to above its critical temperature and pressure results in a supercritical fluid. The density is intermediate between a liquid and a gas and can be varied as a function of temperature and pressure. Hence, the solubility of supercritical fluids can be tuned so that selective extractions can be obtained. Due to the gas like properties, rapid extractions can be accomplished compared to liquid extractions as the diffusion rates are higher. $CO_2$ is a commonly utilized supercritical fluid as its critical parameters can easily be reached. For example, one report has demonstrated a low yield of krill phospholipids by using supercritical fluid extraction at a pressure of 500 bar and a temperature of 100° C. Yamaguchi (1986). A second report provides data on specific process conditions, which include pressure and temperature ranges (e.g., 300 to 500 bar and 60 to 75° C.). These data are from a pilot scale process wherein an extraction of 84 to 90% of krill total lipids was achieved. Bruheim et al., United States Patent Application Publication Number 2008/0274203 (herein incorporated by reference).

Supercritical $CO_2$ is also non-flammable, cheap and inert, wherein such factors are relevant when considering industrial applicability. The inertness results in low grade of oxidation of labile compounds during extraction. $CO_2$ also has a low surface tension which is advantage so that the extraction medium can penetrate the material efficiently. In order to extract more polar substances, the $CO_2$ can be mixed with a polar solvent such as ethanol. The level of modifier can be varied to provide extra selectivity as well.

Consequently, currently available industrial scale supercritical fluid extraction processes using high temperatures and pressures has resulted in a low extraction efficiency of conventional krill meal thereby providing an insufficient oil yield to provide a commercially feasible solution for krill extraction. Further, these currently available extraction processes do not solve the problems discussed herein regarding providing improved low fluoride meal and/or oil compositions.

Therefore, the improved solvent extraction methods described herein have been developed. In one embodiment, co-solvents are used with the supercritical CO2, either alone or in various combinations of ethanol, hexane, acetone. For example, if ethanol is used alone as an extraction solvent, it has been observed that krill material is less selective than extraction with supercritical $CO_2$. Pronova et al., WO 2008/060163 A1. As a result, undesirable substances are extracted into the krill oil resulting in a need for additional post-extraction clean-up/processing. Further, ethanol-only extracted krill oil tends to have higher viscosity and darker color which is independent of astaxanthin content of the oil.

In some embodiments, the present invention contemplates methods that have unexpected findings including but not limited to: i) PPC was extracted using low pressures (i.e., for example, between approximately 177 to 300 bar) and low temperatures (i.e., for example, between approximately 33 and 60° C.); and ii) high yield of lipid extract was produced (data available). It appears that krill meal consisting of hydrolyzed protein allows for easier extraction of the associated lipids in particular the phospholipid rich fraction of krill oil.

The data presented herein demonstrates that supercritical CO2 was found to be a selective extraction method as it produced high purity extracts containing triglycerides, phospholipids and astaxanthin with minimal brown color and superior organoleptic quality as compared to krill oils produced by ethanol-only extraction and/or acetone+ethanol extraction. Brown color of krill oil is considered to be undesirable. The exact origin of the brown color is unknown but it is believed to be associated with oxidation of krill lipids during the manufacture of krill meal phospholipids and/or degradation of the carotenoid astaxanthin.

The properties of such a supercritical fluid can be altered by varying the pressure and temperature, allowing selective component extraction. Extraction conditions for supercritical $CO_2$ are above the critical temperature of 31° C. and critical pressure of 74 bar. Addition of modifiers may slightly alter these values. For example, neutral lipids and cholesterol can be extracted from egg yolk with $CO_2$ pressures up to 370 bar and temperature up to 45° C., while using higher temperature, e.g. 55° C., would result in increased rate of phospholipid extraction. $CO_2$ has a high industrial applicability because it is non-flammable, cheap and inert. The inertness results in low oxidation of labile compounds during extraction.

As mentioned, the supercritical $CO_2$ is fluid. Its density is intermediate between a liquid and a gas and can be varied as a function of temperature and pressure. Hence, the solubility of supercritical fluids can be tuned so that selective extractions can be obtained. Due to the gas-like properties, rapid extractions can be accomplished compared to liquid-extractions. In the present method the extraction is effective; even 95% of the krill oil existing in the PPC is separated. Although it is not necessary to understand the mechanism of an invention, it is believed that the phospholipids of the feed material are embedded in a matrix of hydrolyzed protein which means that the close association between the phospholipids and hydrophobic/phosphorylated proteins is broken thus facilitating the extraction of the lipids. In addition, a minimal amount of fluoride content is transferred to oil during the $CO_2$ extraction process. For example, the fluoride content of PPC is about 0.3 g/kg, but after the $CO_2$ extraction the fluoride content of the krill oil is less than 0.5 mg/kg.

Alternatively, when using only supercritical $CO_2$ as solvent (step 19), triglycerides and/or neutral oil may be separated from the PPC composition subfraction. In one embodiment, supercritical $CO_2$-only extraction generates a low fluoride 'de-oiled PPC' composition. Although it is not necessary to understand the mechanism of an invention, it is believed that de-oiled PPC is the most valuable portion of the PPC composition subfraction. When thereafter, the de-oiled PPC composition may be extracted using ethanol as a solvent (see, step 1A), wherein a phospholipid subfraction and a protein hydrolysate fraction is also generated.

Figure 3:
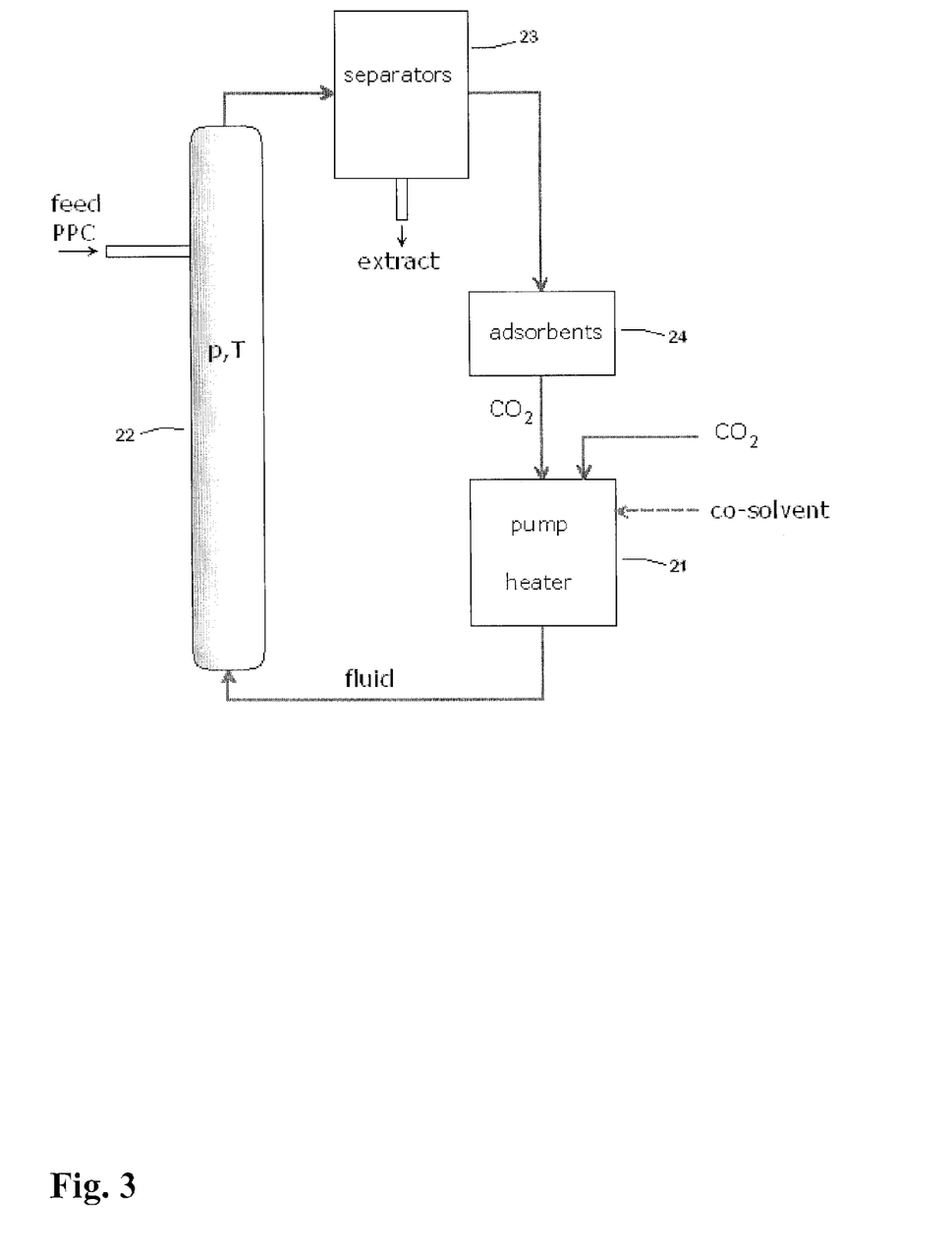
FIG. 3 depicts one example of an extraction plant suitable for use in the presently disclosed method. For example, the plant comprises a solvent unit (21), an extraction tank (22), separators (23) and adsorbents (24).
Figure 4:
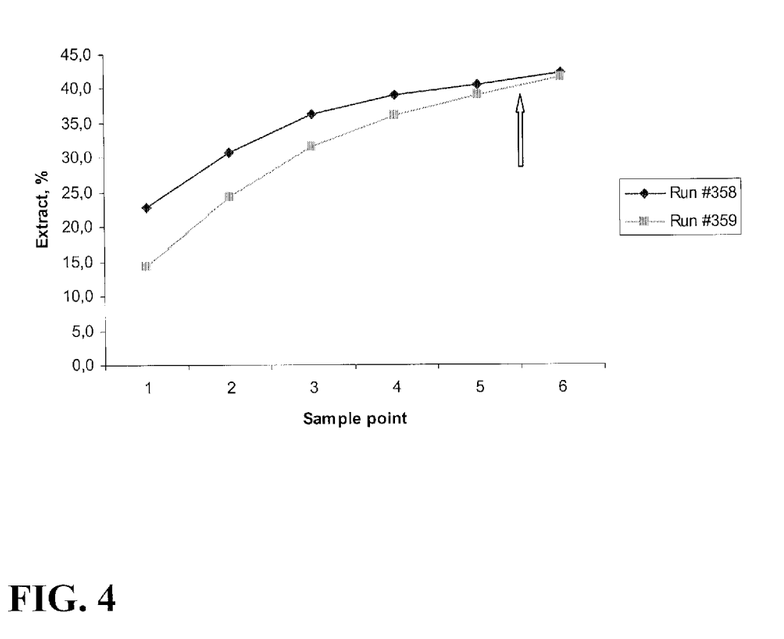
FIG. 4 present exemplary data showing the extraction efficiencies of two different runs in accordance with one embodiment of the present invention.

In one embodiment, the present invention contemplates a system comprising an extraction plant, including but not limited to, a solvent unit 21, vertical tank 22, separators 23 and adsorbents 24. See, FIG. 3. Normal $CO_2$ and possible co-solvent are fed to the solvent unit, which contains i.a. a pump to generate a certain pressure p and a heater to generate a certain temperature T. The supercritical $CO_2$ with possible co-solvent are then fed to the lower end of the tank 22. The feed material, in this case the PPC, is fed to the tank by means of own pump. Material affected by the solvent flows out of the upper end of the tank. The separators 22 separate the extract result, for example krill oil, to output of the system. If ethanol is used as co-solvent, it follows the extract proper and has to be evaporated away. The $CO_2$ continues its circulation to adsorbents 23, where it is cleaned, and thereafter back to the solvent unit 21.

EXPERIMENTAL

Example I

Production of Low Fluoride Krill Oil 5 kg batches of PPC feed material in granular form was processed using $CO_2$ as solvent and azeotropic food grade ethanol as co-solvent, the weight of the ethanol being 23% of the weight of $CO_2$. The plant was pre-pressurised to operating pressure with $CO_2$ only, and ethanol was added when $CO_2$ circulation started. Solvent to feed material ratio was 25:1 or greater and co-solvent to feed material ratio was 5:1. Runs were carried out under two extraction conditions; 300 bar at 60° C., and 177 bar at 40° C. See, Table II.

TABLE II

| Extraction conditions | | |
|---|---|---|
|  | Run 1 | Run 2 |
| Feed Mass (g, as received) | 5000.5 | 5000.9 |
| Extraction pressure (bar) | 300 | 177 |
| Extraction temperature (° C.) | 60 | 33 |
| First separator pressure (bar) | 90 | 90 |
| First separator temperature (° C.) | 41 | 41 |
| Second separator pressure (bar) | 48-50 | 48-50 |
| Second separator temperature (° C.) | 39 | 39 |
| $CO_2$ used with ethanol co-solvent (kg) | 132.6 | 134.9 |
| Additional $CO_2$ at end of run (kg) | 33.1 | 44.5 |
| Total ethanol used (kg) | 31.65 | 32.19 |

The extracted material was passed through two separation vessels in series, held at 90 bar and 45-50 bar respectively. Material collected from both separators was pooled together for evaporation of ethanol.

The feed material, 'Emerald krill meal' granules (Olymeg or PPC), were supplied in a sealed plastic bag containing approximately 25 kg. The feed material was kept frozen until used in extractions. The granules have a size distribution typically in the range 2 to 5 mm, but a number of fine fragments were also present. The granules are greasy to the touch but still break up under compression rather than smear.

Extraction results: Table III gives the mass of each extract sample from the two runs, and curves below the table show the cumulative extraction. A total yield of 41-42 wt % of the feed material was achieved for all runs. The runs carried out at 300 bar and 60° C. had a higher initial rate of extraction. The extraction curves indicate that the extraction is virtually complete after sample point 5 where the cumulative $CO_2$ use was 21.5 to 22.0 kg of $CO_2$/kg feed. Estimated maximum extraction is achieved at a point where the $CO_2$:feed ratio is 26.5:1. See, FIG. 3 (estimated maximum extraction is marked by an arrow). The ratio of azeotropic ethanol to $CO_2$ was 0.24:1 for the 300 bar runs, and slightly higher at 0.26:1 for the lower pressure run.

TABLE III

| Progressive extract sample points and yields. | | | | | | | |
|---|---|---|---|---|---|---|---|
|  | Sample | | | | | | |
|  | 1 | 2 | 3 | 4 | 5 | 6 | Total |
| Run 1 | | | | | | | |
| Cumulative $CO_2$ (kg/kg feed) | 5.5 | 9.1 | 13.4 | 17.8 | 22.0 | 33.1 | |
| Extracted oil (g, dry) | 1137 | 398 | 282 | 135 | 78 | 86 | 2115 |
| Run 2 | | | | | | | |
| Cumulative $CO_2$ (kg/k feed) | 5.6 | 9.1 | 13.5 | 17.5 | 21.5 | 34.4 | |
| Extracted oil (g, dry) | 715 | 496 | 368 | 220 | 149 | 129 | 2077 |

Near complete extraction of total lipids was achieved, with average yield of 95% of total lipids and 90% of phospholipids. The final yield was similar for both the high and low pressure runs, but neutral lipids were more rapidly extracted at higher pressure. The phospholipid extraction rate was similar under both extraction conditions. The combined extract had an overall phospholipid level of just over 40 wt %. Phosphatidyl inositol and phosphatidyl serine were poorly extracted.

Phospholipid profiles of the lipid extracts are given in Table IV. First column shows the phospholipid profile of the feed material (PPC or 'Olymeg®') and the last two columns show the phospholipid profiles of the extracted PPC residue sampled from top and bottom of the extraction column. In the lipid extracts the major phospholipid is phosphatidyl choline (PC) with proportion ranging from 72.7% to 80.4% including alkyl acyl phosphatidyl choline (AAPC) and lyso forms of the PCs (LPC and LAAPC). Smaller amounts of phosphatidyl ethanolamine (PE) are present in the feed material (5.3%) and in the lipid extracts (3.5-4.5%). Alkyl acyl and lyso forms of PE (AAPE, LPE) are also present in the feed material and lipid extracts. Phosphatidyl inositol (PI) and phosphatidyl serine are present in the feed material (PPC), but because they are poorly soluble in ethanol, these phospholipids are concentrated in the PPC residue.

TABLE IV

Phospholipid Profiles Of Lipid Extracts (run 1)

| Sample | Olymeg 10071199 | Extract 1 | Extract 2 | Extract 3 | Extract 4 | Extract 5 | Extract 6 | Residue (Top) | Residue (Bottom) |
|---|---|---|---|---|---|---|---|---|---|
| | | | | Wt % of total PL | | | | | |
| PC | 70.1 | 80.4 | 77.1 | 76.9 | 75.9 | 73.5 | 72.7 | 40.2 | 32.5 |
| AAPC | 8.5 | 8.0 | 9.0 | 9.8 | 9.1 | 10.6 | 9.0 | 7.5 | 7.8 |
| PI | 1.8 | | | | 0.7 | 0.6 | 0.6 | 6.2 | 10.1 |
| PS | 1.0 | | | | | | | 5.5 | 8.1 |
| LPC | 6.9 | 4.6 | 5.6 | 5.7 | 6.0 | 6.8 | 7.5 | 13.4 | 8.9 |
| LAAPC | 1.7 | 1.2 | 1.2 | 1.0 | 1.3 | 1.2 | 1.4 | 3.2 | 2.6 |
| PE | 5.3 | 3.6 | 4.0 | 3.5 | 3.8 | 3.5 | 4.5 | 9.4 | 9.4 |
| EPLAS | 0.6 | 0.0 | 0.5 | 0.5 | 0.5 | 0.5 | 0.3 | 1.0 | 2.2 |
| AAPE | 2.0 | 1.1 | 1.5 | 1.3 | 1.6 | 1.6 | 2.0 | 4.4 | 4.9 |
| LPS | | | | | | | | 0.7 | 1.9 |
| CL/NAPE | 1.0 | 0.9 | 0.7 | 0.8 | 0.8 | 1.2 | 1.6 | 4.2 | 5.7 |
| LPE | 0.8 | 0.3 | 0.4 | 0.4 | 0.4 | 0.4 | 0.4 | 3.2 | 4.5 |
| Total PL (wt % of lipid) | 40.88 | | | | | | | 81.46 | 80.96 |
| Lipid yield (wt %) | 44.7 | | | | | | | 4.9 | 5.9 |
| Total PL (wt % of sample) | 18.3 | 26.68 | 46.03 | 57.94 | 71.34 | 76.13 | 78.50 | 4.0 | 4.8 |

The results presented in Table V (below) show that no free fatty acids (FFAs) are present in the lipid extracts. Sterols are present at levels of 2% or less in the extract. Triglycerides (TAGs) were measured at around 40 wt % and phospholipids (e.g., polar lipids) at around 50% in the extracts. See, Table V.

TABLE V

Main Components Of The Lipid Extracts

| | TAG | Polar lipid | Sterols | FFA | Astaxanthin | Total lipid |
|---|---|---|---|---|---|---|
| Run 1 | 40.3 | 46.9 | 1.9 | ND | 0.05 | 92.2 |
| Run 2 | 42.1 | 50.2 | 2 | ND | 0.05 | 95.3 |

The method and products according to the invention has been described above. The method can naturally vary in its details from those presented. The inventive idea may be applied in different ways within the limits set by the independent claim 1.

Example II

Extraction Efficiency

This example demonstrates an exemplary analytical extraction with the Soxhlet method.

The neutral lipids are often part of large aggregates in storage tissues, from which they are relatively easily extracted. The polar lipids, on the other hand, are present as constituents of membranes, where they occur in a close association with proteins and polysaccharides, with which they interact, and therefore are not extracted so readily. Furthermore, the phospholipids are relatively tightly bound with hydrophobic proteins and in particular with the phosphorylated proteins.

Partial hydrolysis of the protein matrix in the novel krill meal improves the extraction efficiency of total lipid by use of organic solvents as demonstrated by this example involving extraction of krill meal samples with the Soxhlet method by using petroleum ether as solvent. Soxhlet method is a standard method in quantitative determination of fat content of foods and feeds and thus it can be used as a reference method to determine the extractability of various krill meals.

Extraction according to the Soxhlet method was carried out using petroleum ether (boiling point 30-60° C.) to evaluate the extraction capacity using $SC-CO_2$. Briefly, a 10 g sample of milled krill meal was weighed and placed in a Soxhlet apparatus and then continuously extracted for approximately eight (8) hours using 300 mL petroleum ether. After extraction, the solvent was evaporated at 60° C. under a nitrogen stream. Soxhlet F., "Die gewichtsanalytische bestimmung des milchfettes" *Dingler's Polytech. J.* 232:461-465 (1879). Conventional krill meal was prepared as described in US 2008/0274203 (Aker Biomarine ASA, Bruheim et al.) and the novel krill meal was prepared according to the present invention.

The results show that the proportion of residual (e.g., un-extracted) lipid was twice as large in the conventional krill meal compared to the novel krill meal. See, Table VI.

TABLE VI

| Extracted material | Extracted lipid | Residual lipid |
|---|---|---|
| Conventional krill meal | 79.6% | 20.4% |
| Novel krill meal | 88.9% | 11.1% |

Consequently, the extraction methods described herein have provided an unpredictable and surprising result that provides a superior product because of a greatly improved extraction efficiency.

Example III

Determination of Fluoride Content

This example presents one method of determining fluoride content of krill products as fluoride by chemical analysis using an ion selective electrode.

The samples analyzed were krill meal and oil extracted from the said krill meal. The krill meals analyzed for fluoride content were produced by: i) a low fluoride method of present invention; and ii) a whole krill material produced by a conventional process. As explained herein, the method disclosed herein removes, in most part, the krill exoskeleton while the krill shell is included in the meal prepared from whole krill according to the conventional process. Conventional processes are, for example, described in WO 2002/102394 (Neptune Technologies & Bioresources) and US 2008/0274203 (Aker Biomarine ASA).

The data demonstrate that by removing the exoskeleton in the process of producing krill meal, the fluoride content of the meal and the oil produced from the meal have a markedly reduced fluoride content. See, Table VII.

TABLE VII

Fluoride Content Comparison To Conventional Processes

|  | Process of present invention | Conventional process |
|---|---|---|
| Krill meal | 300-500 ppm | 1300 ppm |
| Krill oil | <0.5 ppm | 0.5-5 ppm |

Example IV

Krill Oil Color Comparison

Krill oil has typically a strong red colour arising from the carotenoid astaxanthin present in the oil at levels varying from 50 ppm to 1500 ppm. Color of krill oil can be determined with a LabScan® XE spectrophotometer (Hunter Associates Laboratory, INC. Resbon, Va., USA) and reported in CIELAB colour scales (L*, a* and b* values). Deviation from the red colour of astaxanthin can occur when the krill biomass is processed at high temperature and under conditions that induce oxidation. Typical oxidation induced deviation in krill oil color is an increase in the brownish hue. Brown color in krill oil arises from oxidation of lipids and formation of secondary and tertiary oxidation products with amino residues. This process is also called non-enzymatic browning.

Strecker degradation products and pyrroles are products of non-enzymatic browning that have been characterized in samples of krill oil. For example, polymerization of pyrroles results in formation of brown, melatonin like macromolecules. Furthermore, pyrrole content of krill oil can be determined spectroscopically with absorbance at 570 nm.

Samples of three krill oils will be examined for color. One produced by the method of the present invention, one produced from frozen krill by a method described in WO 2002/102394 (Neptune Technologies & Bioresources) and one extracted from dried krill meal with ethanol alone as described in US 2008/0274203 (Aker Biomarine ASA). It is to be found that krill oil produced by the method of the present invention has the lowest level of brown color determined spectrophotometrically by using CIELAB colour scales (L*, a* and b* values) and/or the lowest level of pyrroles determined spectroscopically.

Example V

Organoleptic Krill Oil Quality Determination

Organoleptic quality of krill oil is conventionally determined by chemical analysis of volatile nitrogenous compounds arising from the decomposition of krill proteins and trimethyl amine oxide (TMAO). Nitrogenous compounds analyzed are total volatile nitrogen (TVN) and trimethylamine (TMA). In simplified terms the level of nitrogenous compounds correlate with the level of spoilage in the raw material i.e. krill biomass used for extraction of the oil.

It has become evident that, in addition to the volatile nitrogenous compounds, a large number of volatile components with distinct odour contribute to the sensory properties of krill oil. Many of the volatile components arise from the oxidation of lipid and proteinaceous compounds of krill biomass. Thus, a method that limits the level of oxidative degradation in the krill biomass, will reduce the amount of volatile components in krill oil.

Assessment of the organoleptic quality of different types of krill oil is to be performed by a panel of trained individuals. The sensory properties to be determined include several predefined parameters of smell and taste. It is to be found that the novel krill oil has an improved sensory profile compared to the other oils tested. The other oils to be tested include one extracted from frozen krill by a method described in WO 2002/102394 (Neptune Technologies & Bioresources) and one extracted from dried krill meal with ethanol alone as described in US 2008/0274203 (Aker Biomarine ASA).

We claim:

1. A fluoride-reduced krill oil composition comprising phospholipids that are essentially free of protein and less than approximately 0.5 ppm fluoride.

2. The krill oil of claim 1, wherein said phospholipids comprise at least approximately 40-50 wt % of total lipid.

3. The krill oil of claim 1, further comprising triglycerides and neutral lipids.

4. The krill oil of claim 1, further comprising less than approximately 0.8 wt % free fatty acids.

5. The krill oil of claim 1, further comprising approximately 20-26 wt % Omega-3 fatty acids.

6. The krill oil of claim 1, further comprising approximately 1.5 wt % lysophosphatidic acid.

* * * * *

UNITED STATES PATENT AND TRADEMARK OFFICE
CERTIFICATE OF CORRECTION

| | | |
|---|---|---|
| PATENT NO. | : 9,068,142 B2 | Page 1 of 1 |
| APPLICATION NO. | : 13/856642 | |
| DATED | : June 30, 2015 | |
| INVENTOR(S) | : Inge Bruheim et al. | |

It is certified that error appears in the above-identified patent and that said Letters Patent is hereby corrected as shown below:

In the Claims:

Column 24, line 35, Claim 1, should read as follows:

1. A fluoride-reduced krill oil comprising phospholipids that are essentially free of protein and less than approximately 0.5 ppm fluoride.

Signed and Sealed this
Twenty-second Day of March, 2016

Michelle K. Lee
*Director of the United States Patent and Trademark Office*